United States Patent [19]

Verkaart

[11] Patent Number: 5,417,274
[45] Date of Patent: May 23, 1995

[54] HEATER FOR PHYSIOLOGICAL SOLUTIONS EFFECTIVE AT BOTH LOW AND HIGH FLOW RATES

[76] Inventor: Wesley H. Verkaart, 160 Weymouth St., Rockland, Mass. 02370

[21] Appl. No.: 31,137
[22] Filed: Mar. 12, 1993
[51] Int. Cl.$^6$ .............................................. F28F 27/02
[52] U.S. Cl. .............................. 165/1; 165/103; 165/143
[58] Field of Search ............... 165/103, 143, 155, 1

[56] References Cited

U.S. PATENT DOCUMENTS

| | | | |
|---|---|---|---|
| 569,750 | 10/1896 | Fey | 165/97 |
| 1,040,548 | 10/1912 | Jones | 165/101 |
| 1,267,185 | 5/1918 | Coffman | 165/103 |
| 1,589,281 | 6/1926 | Wittenmeier | 165/103 |
| 1,869,637 | 8/1932 | Walworth | 155/103 |
| 2,053,780 | 9/1936 | Price et al. | 165/143 |
| 2,414,953 | 1/1947 | Johnson | 165/103 |
| 4,759,749 | 7/1988 | Verkaart | . |
| 5,063,994 | 11/1991 | Verkaart | . |
| 5,168,920 | 12/1992 | Brauer et al. | 165/100 |

Primary Examiner—A. Michael Chambers
Attorney, Agent, or Firm—Dickinson, Wright, Moon, Van Dusen & Freeman

[57] ABSTRACT

A heater for physiological solutions that is effective at low and high flow rates includes first and second heat exchangers that have different fluid heating characteristics. The first heat exchanger is capable of heating solutions at high flow rates, while the second heat exchanger is designed to heat the solutions at low flow rates. A warming fluid is circulated through the heat exchangers, and a manifold is provided to control the flow of the warming fluid that is directed to the two heat exchangers. The solution to be warmed is directed to both heat exchangers such that a warmed solution is provided irrespective of the flow rates.

14 Claims, 2 Drawing Sheets

HEATER FOR PHYSIOLOGICAL SOLUTIONS EFFECTIVE AT BOTH LOW AND HIGH FLOW RATES

TECHNICAL FIELD

This invention relates to the art of heat exchangers, particularly heat exchangers used for heating physiological solutions.

BACKGROUND

Heat exchangers that are designed to heat physiological solutions at relatively high solution flow rates, e.g. greater than about 60 ml/min., are known. For example, see my earlier U.S. Pat. No. 4,759,749 where a heat exchanger having an inner tube that carries a warming fluid and an outer tube that forms a channel for the solution to be warmed is described. It is also known to provide a heat exchanger for maintaining the temperature of a physiological solution that is flowing at a substantially lower rate. For example, see my earlier U.S. Pat. No. 5,063,994 where a heat exchanger having a central tube for carrying the solution to be warmed and outer channels for carrying the warming fluid is described.

Heat exchangers such as those described above have been designed to be operated as separate units. That is, each heat exchanger has fluid heating characteristics for particular uses, and each has its own, independent source of warming fluid. While the heat exchangers can be used simultaneously for the same patient, such use is awkward, at best, because of the duplication of various parts, particularly the pumps and reservoirs for the warming fluids. This often means that the physician chooses to use only one of the units, which leads to the patient's receiving (1) heated solutions too slowly, as when the unit having a lower flow rate capability is used even though it is too small, or (2) solutions that are at lower than optimum temperature, as when the unit having a higher flow rate capability is operated at a rate that is too low to maintain temperature in the line to the patient.

SUMMARY OF THE INVENTION

In accordance with the invention, a heat exchanger is provided that utilizes a unique manifold for allowing two types of heat exchangers to operate as a single system and with a single source of warming fluid. In the preferred embodiment, the manifold is attached to the first heat exchanger in such a manner that the manifold and first heat exchanger can be installed into an existing support stand for the first heat exchanger. The second heat exchanger is attached to the first one for receiving a flow of warming fluid from the manifold. The flow of warming fluid is directed to the manifold, and the manifold divides the flow between the two heat exchangers to provide each with a desired rate of flow of the warming fluid.

The manifold is preferably one of two types. The first includes what is commonly known as a "flow nozzle" which provides a precision orifice located between first and second ports. The warming fluid is supplied to the first port from a source of circulating warming fluid, and the second port is connected to the first heat exchanger. A third port in the manifold is connected between the first port and the second heat exchanger. Some of the warming fluid flows from the first port to the second heat exchanger via the third port because of fluid pressure created by the presence of the orifice. After the warming fluid has passed through the second heat exchanger, it is returned to a fourth port that is connected directly to the second port on the downstream side of the orifice. All of the warming fluid is then directed to the first heat exchanger through the fourth port and subsequently returned to the source of warming fluid for recirculation.

The second type of manifold includes what is known as a venturi tube. In this embodiment, a constricted part that forms the throat is provided between the first and second ports, and the fourth port is connected to the throat. As is known in the art, the static pressure is reduced in the throat, thus pulling the warming fluid returning from the second heat exchanger into the second port.

The physiological solution to be warmed is passed through the first heat exchanger, a filter, and the second heat exchanger, preferably countercurrent to the flow of the warming fluid. With this arrangement, the solution is supplied to the patient at the desired temperature for a wide range of flow rates, and easy setup of the system is facilitated.

DETAILED DESCRIPTION OF THE DRAWINGS

Figure 1:
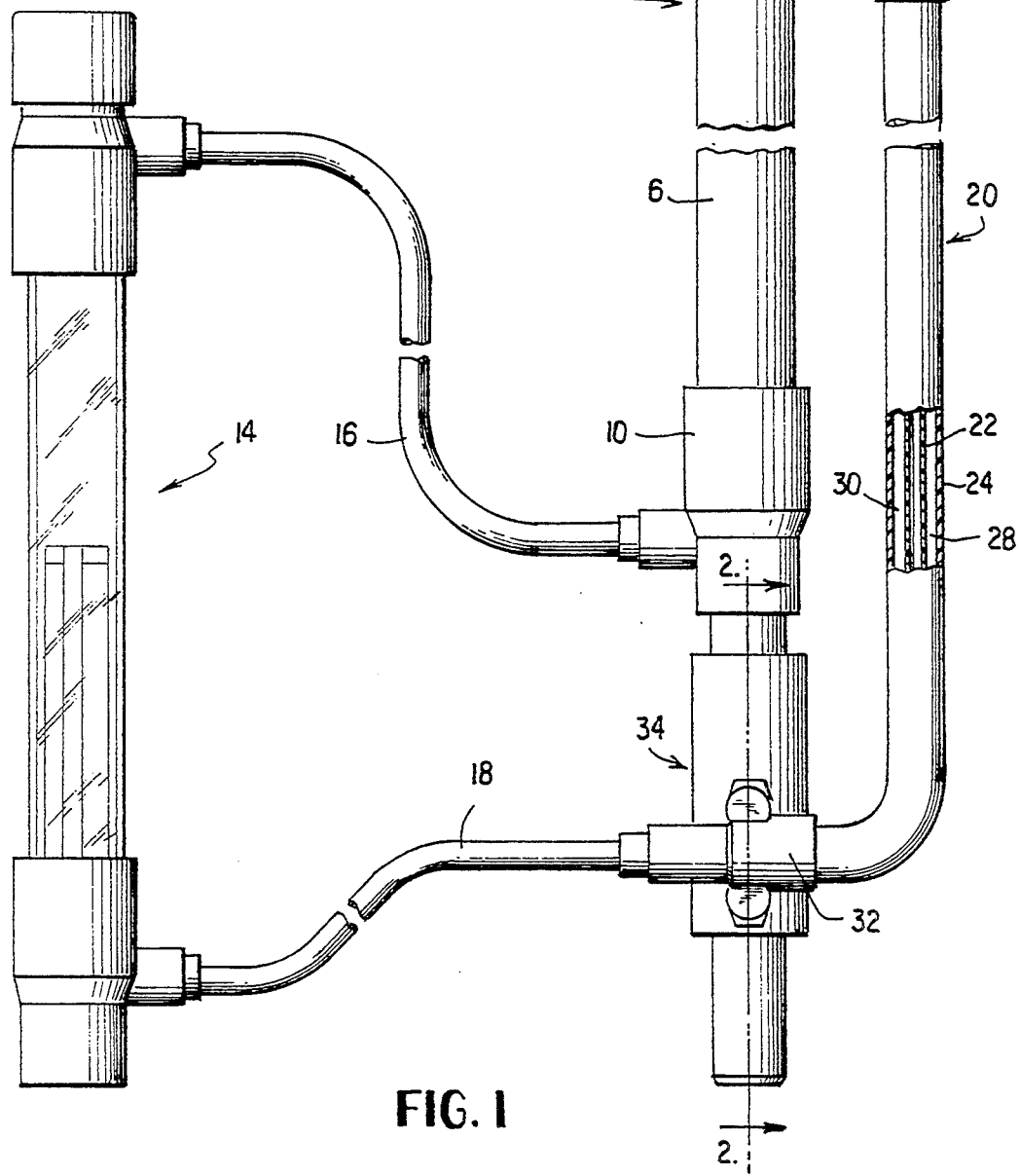
FIG. 1 is a side view of a preferred embodiment of the invention.

With reference to FIG. 1 of the drawings, a first heat exchanger 2 is of the type shown in U.S. Pat. No. 4,759,749. Heat exchanger 2 comprises an inner tube 4, an outer tube 6, and end caps 8 and 10. The inner tube 4 forms a passage for a warming fluid, and a physiological solution to be warmed is introduced through tubing 12 to a helical passage formed between the inner and outer tubes. After warming in heat exchanger 2, the physiological solution is supplied through tube 16 to a particulate filter 14. The outlet of the filter 14 is directed through tube 18 to the solution inlet of a second heat exchanger 20. The second heat exchanger 20 is of the type described in U.S. Pat. No. 5,063,994 and comprises a central tube, or passageway 22 for carrying a solution to be warmed, an outer tube 24 for carrying a warming fluid in thermal contact with the solution, and an end cap 26. The outer tube forms a first flow channel 28 for carrying a warming fluid toward end cap 26 and a second flow channel 30 for carrying warming fluid returning from end cap 26. End cap 26 reverses the flow of the warming fluid as is described in the noted U.S. Patent.

The solution to be warmed is introduced to central tube 22 at a connector 32, which is similar to that described in U.S. Pat. No. 5,063,994.

Figure 2:
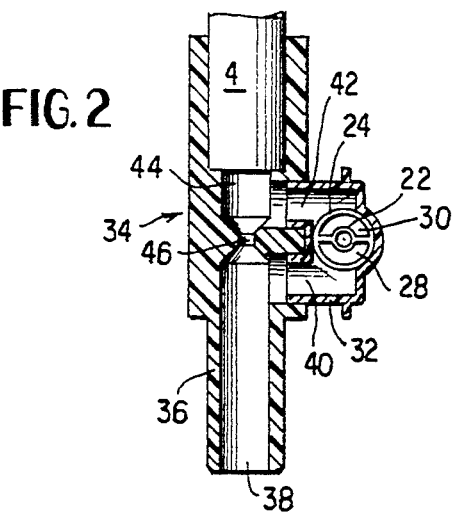
FIG. 2 is a cross section taken along line 2—2 of FIG. 1.

FIG. 2 is a cross section taken along line 2—2 of FIG. 1 and shows manifold 34 in greater detail. The manifold includes a nipple 36 for engaging a fluid connector as described in U.S. Pat. No. 4,759,749 for supplying a temperature controlled warming fluid from a reservoir (not shown) to a passageway 38. Some of the warming fluid is directed to the second heat exchanger 20 through port 40, which in turn communicates with flow channel 28. Warming fluid returning by way of flow channel 30 is directed into port 42, which is in turn connected to port 44. Warming fluid in port 44 is directed to tube 4 of heat exchanger 2 for passage therethrough and return to the source of warming fluid.

Ports 38 and 44 are in direct fluid communication with each other, but orifice 46 is located between these ports. The orifice 46 places a restriction in the flow of fluid between ports 38 and 44 and thereby creates the difference between the pressures in the ports that is required to direct a desired amount of the warming fluid through the channels 28 and 30.

Figure 2A:
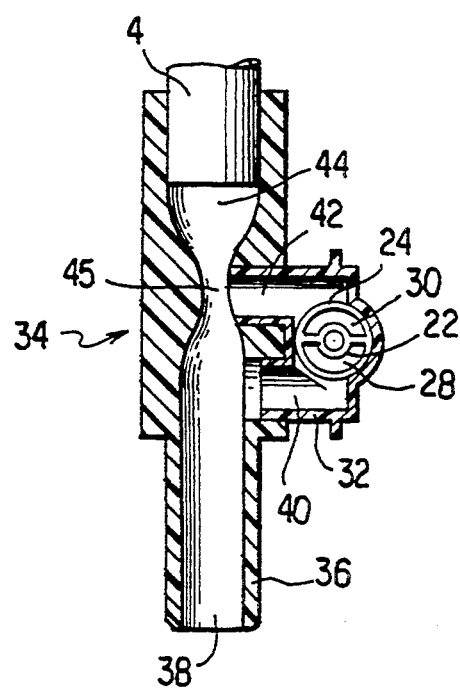
FIG. 2a is a cross section similar to that of FIG. 2 showing another embodiment of a manifold.

A second embodiment of the manifold 34 is shown in FIG. 2a. According to this embodiment, a venturi tube in provided having a throat portion 45. The port 42, which carries warming fluid returning from the second heat exchanger, is connected to the throat 45. The pressure in the throat is reduced by the increased flow velocity in the throat, and this pulls the warming fluid through the second heat exchanger efficiently. Of course, the dimensions of the ports and the throat can be designed to provide the desired flow rates.

The heat transfer characteristics of heat exchanger 2 differ from those of heat exchanger 20. Heat exchanger 2 is designed to heat solutions at a relatively high flow rate, whereas heat exchanger 20 is designed to serve as a heated patient line for maintaining the temperature of solutions up to the point at which they are admitted to a patient when flowing at a relatively low rate. This combination is effective because the temperature of a fluid flowing at a large rate does not require the addition of heat from the heat exchanger 20, whereas a fluid flowing at a lower rate would normally cool in the patient line and does require heat from the heat exchanger 20 to maintain its temperature.

Modifications within the scope of the appended claims will be apparent to those of skill in the art.

I claim:

1. A method for heating a solution and maintaining the temperature of said solution comprising supplying said solution to the first heat exchange portion of a heat exchange apparatus having first and second heat exchange portions for heating said solution to a desired temperature and at a first rate of heating, supplying said solution to said second heat exchange portion for maintaining said solution at said desired temperature, providing one of said first and second heat exchange portions with a warming fluid for thermal contact with said solution to be heated, providing the other of said first and second heat exchange portions with said warming fluid that has passed at least partially through said one of said first and second heat exchange portions for thermal contact with said solution to be heated and returning said warming fluid from said other heat exchange portion to said one of said heat exchange portions.

2. A method according to claim 1 wherein said step of supplying comprises supplying a physiological solution to said first heat exchanger at a temperature below normal body temperature and said desired temperature comprises substantially normal body temperature.

3. A method according to claim 1 wherein said step of providing comprises providing only a portion of said warming fluid to said one of said first and second heat exchangers.

4. A heat exchange apparatus comprising a first heat exchanger having an inner tube for carrying a first fluid and an outer tube for carrying a second fluid in thermal contact with said first fluid and means for directing at least a portion of said first fluid into a flow channel of a second heat exchanger and for returning said portion of said first fluid from said flow channel to said inner tube.

5. Apparatus according to claim 1 wherein said inner tube includes a first end for being removably received in a first fluid connector for supplying said first fluid to said inner tube and a second end for being received in a second fluid connector for discharging said first fluid.

6. Apparatus according to claim 5 further comprising means for directing said second fluid to a passageway for thermal contact with said first fluid in said flow channel.

7. Apparatus according to claim 6 wherein said means for diverting comprises restriction means for restricting flow in said inner tube, an inlet port for said flow channel on one side of said restriction means and an outlet port for said flow channel on an opposite side of said restriction means.

8. Apparatus according to claim 6 wherein said means for diverting comprises venturi means forming a throat, an inlet port for said flow channel on one side of said throat and an outlet port for said flow channel in fluid communication with said throat.

9. A heat exchange apparatus comprising a first heat exchange portion and a second heat exchange portion, wherein said first heat exchange portion comprises first means for carrying a warming fluid and first means for carrying a solution to be warmed in thermal contact with said warming fluid and said second heat exchange portion comprises second means for carrying said warming fluid and second means for carrying a solution to be warmed in thermal contact with said warming fluid, and said heat exchange apparatus further comprises means for directing said solution to be warmed from first means for carrying a solution to be warmed to said second means for carrying a solution to be warmed and means for diverting at least a portion of said warming fluid from said first means for carrying a warming fluid to said second means for carrying a warming fluid and for returning said portion of said warming fluid to said first means for carrying a warming fluid.

10. A combination according to claim 9, wherein said first means for carrying a warming fluid includes an inlet port for receiving said warming fluid and an outlet port for discharging said warming fluid, and said means for diverting obtains and returns said portion between said inlet port and said outlet port.

11. A combination according to claim 10 wherein said inlet and said outlet each comprises means for removably receiving a respective fluid connector.

12. A combination according to claim 9 wherein said first heat exchange portion is capable of transferring heat to said solution to be warmed at a first rate and said second heat exchange portion is capable of transferring heat to said solution to be warmed at a second rate that differs from said first rate.

13. A combination according to claim 12 wherein said first rate is larger than said second rate.

14. A combination according to claim 13 wherein said solution to be heated is a physiological solution, said first heat exchanger is for receiving said physiological solution substantially below normal body temperature and heating said physiological solution to substantially body temperature, and said second heat exchanger is a heated patient line for maintaining the temperature of said physiological solution at substantially normal body temperature.

* * * * *